(12) United States Patent
Pond et al.

(10) Patent No.: US 9,821,007 B2
(45) Date of Patent: Nov. 21, 2017

(54) DENTAL IRRIGANT

(71) Applicant: Inter-Med, Inc., Racine, WI (US)

(72) Inventors: Gary J. Pond, Milwaukee, WI (US); Thomas V. Kandathil, Racine, WI (US)

(73) Assignee: Inter-Med, Inc., Racine, WI (US)

( * ) Notice: Subject to any disclaimer, the term of this patent is extended or adjusted under 35 U.S.C. 154(b) by 0 days.

(21) Appl. No.: 14/984,167

(22) Filed: Dec. 30, 2015

(65) Prior Publication Data

US 2016/0184352 A1  Jun. 30, 2016

Related U.S. Application Data

(63) Continuation of application No. 12/217,601, filed on Jul. 7, 2008, now Pat. No. 9,233,262, which is a continuation of application No. 11/998,972, filed on Dec. 3, 2007, now abandoned.

(60) Provisional application No. 60/872,107, filed on Dec. 1, 2006.

(51) Int. Cl.
| | |
|---|---|
| *A01N 47/44* | (2006.01) |
| *A01P 1/00* | (2006.01) |
| *A01N 59/00* | (2006.01) |
| *A61K 33/20* | (2006.01) |
| *A61K 8/02* | (2006.01) |
| *A61K 8/20* | (2006.01) |
| *A61K 8/43* | (2006.01) |
| *A61K 8/70* | (2006.01) |
| *A61Q 11/00* | (2006.01) |
| *A61Q 17/00* | (2006.01) |
| *A01N 25/02* | (2006.01) |
| *A61K 9/08* | (2006.01) |
| *A61K 31/155* | (2006.01) |
| *A61K 33/00* | (2006.01) |

(52) U.S. Cl.
CPC .............. *A61K 33/20* (2013.01); *A01N 25/02* (2013.01); *A01N 47/44* (2013.01); *A01N 59/00* (2013.01); *A61K 8/0208* (2013.01); *A61K 8/20* (2013.01); *A61K 8/43* (2013.01); *A61K 8/70* (2013.01); *A61K 9/08* (2013.01); *A61K 31/155* (2013.01); *A61K 33/00* (2013.01); *A61Q 11/00* (2013.01); *A61Q 17/005* (2013.01)

(58) Field of Classification Search
None
See application file for complete search history.

(56) References Cited

U.S. PATENT DOCUMENTS

| | | | |
|---|---|---|---|
| 4,919,837 A | 4/1990 | Gluck | |
| H001467 H | 8/1995 | Prieto | |
| 5,624,891 A | 4/1997 | Smialowicz | |
| 5,719,113 A * | 2/1998 | Fendler | ............ A61K 8/39 510/123 |
| 5,739,168 A | 4/1998 | Hioki | |
| 6,190,542 B1 | 2/2001 | Comolli | |
| 6,190,642 B1 | 2/2001 | Dougherty | |
| 6,255,267 B1 | 7/2001 | Nayar | |
| 6,323,171 B1 | 11/2001 | Fonsny | |
| 6,784,145 B2 | 8/2004 | Delambre | |
| 7,063,793 B2 | 6/2006 | Albiston | |
| 7,070,737 B2 | 7/2006 | Bains | |
| 7,081,246 B2 | 7/2006 | Asmus | |
| 2003/0100465 A1* | 5/2003 | Kilkenny | ............... A01N 33/12 510/384 |
| 2006/0241011 A1 | 10/2006 | Renfrow | |
| 2006/0257281 A1* | 11/2006 | Weide | ................... A61K 31/00 422/6 |

FOREIGN PATENT DOCUMENTS

| | | | | |
|---|---|---|---|---|
| DE | WO 2005056741 A1 * | 6/2005 | ............. | A61K 31/00 |
| WO | 03/061506 | 7/2003 | | |

OTHER PUBLICATIONS

Abou-Rass et al, "The effects of decreasing surface tension on the flow of irrigating solutions in narrow root canals," 1982, Oral Surg., 53(5), 524-526.
Cameron, "The effect of a fluorocarbon surfactant on the surface tension of the endodontic irrigant, sodium hypochlorite," 1986, 31(5), 364-268.
Jeansonne et al, "A comparison of 2.0% chlorhexidine gluconate and 5.25% sodium hypochlorite as antimicrobial endodontic irrigants," 1994, Joe, 20(6), 276-278.
Palazzi et al, "Comparison of the surface tension of 5.25% sodium hypochlorite solution with three new sodium hypochlorite-based endodontic irrigants," 2011, International Endodontic Journal, 1-7.
Shen et al, "Antimicrobial efficacy of chlorhexidien against bacteria in biofilms at different stages of development," 2011, Joe, 37(5), 657-661.
Shen et al, "The synergistic antimicrobial effect by the mechanical agitation and two chlorhexidine preparations on biofilm bacteria," 2010, Joe, 36(1), 101-104.
Shen et al, "Evaluation of the effect of two chlorhexidine preparations on biofilm bacteria in vitro: a three-dimensional quantitative analysis," 2009, Joe, 35(7), 981-985.
Stojicic et al, "Tissue dissolution by sodium hypochlorite: effect of concentration, temperature, agitation, and surfactant," 2010, Joe, 36(9), 1558-1562.
Williamson et al, "Antimicrobial susceptibility of monoculture biofilms of a clinical isolate of Enterococcus faecalis," 2009, Joe, 35(1), 95-97.

* cited by examiner

*Primary Examiner* — Susan Tran
*Assistant Examiner* — William Craigo
(74) *Attorney, Agent, or Firm* — Quarles & Brady LLP (57) ABSTRACT

An irrigant comprising either a hypochlorite compound or a chlorhexidine compound in combination with at least one surfactant and preferably two or more surfactants, including fluorosurfactants, ethoxylates, sulfonates, quaternary ammonium compounds, amine oxides, and combinations thereof, wherein each of the surfactants are capable of complexing with one another.

8 Claims, 7 Drawing Sheets

DENTAL IRRIGANT

RELATED APPLICATIONS

This a continuation patent application of U.S. patent application Ser. No. 12/217,601, filed 7 Jul. 2008, which will issue as U.S. Pat. No. 9,233,262 on Jan. 12, 2016, which is a continuation of U.S. patent application Ser. No. 11/998,972, filed 3 Dec. 2007, now abandoned, which claimed the benefit of U.S. Provisional Patent Application Ser. No. 60/872,107, filed 1 Dec. 2006.

BACKGROUND OF THE INVENTION

The present invention relates to irrigants and disinfectants for surfaces and, more specifically, irrigants and disinfectants used for dental and medical procedures and situations.

Dentists, dental surgeons and dental hygienists and their patients are well aware of the importance of meticulously sterilizing and disinfecting dental instruments. Indeed, since dental instruments are used directly in a patient's mouth, sometimes for invasive or surgical procedures, it is of paramount importance to minimize the presence of microorganisms carried by dental instruments. The microorganisms can range from relatively harmless bacteria to dangerous pathogens. Consequently, efforts are deployed to remove microorganisms from dental instruments and from the fresh water lines feeding dental instruments such as air/water syringes, high speed turbines, and ultrasonic scalers, or from saliva evacuation lines.

Sodium hypochlorite is universally used as an antiseptic for root canal irrigation, its principal functions in root canal treatment being microbicidal, dissolving organic material, and lubrication. However, a disadvantage of sodium hypochlorite is that it is highly toxic to human tissues and cells in concentrated form and corrosive and potentially dangerous to humans at the concentrations at which it is at its most effective as an irrigating medium. Consequently, solutions having low concentrations of sodium hypochlorite are generally used, which results in using larger quantities of solution than what would be considered ideal quantities of the solution.

Similarly, solutions tend to lose their useful properties over time. The additives and agents that compose these solutions tend to oxidize rather quickly once they are subjected to normal environments and surroundings, which causes the strengths of solutions to deteriorate over time and to lose activity. While this deterioration is not necessarily detrimental for everyday household cleaning and disinfecting, it is more pertinent when working with and around skin and tissue. Nonetheless, more stable compounds and solutions are still useful in all situations.

Biofilms

Adhesion to surfaces is a common and well-known behavior of micro-organisms in many habitats, specifically habitats where water or other fluids may be present. This adhesion and the subsequent microbial growth lead to the formation of biofilms. Bacterial biofilms promote increased biomass deposition, resulting in surfaces and environments that are less than desirous regarding sterility and cleanliness.

Treatment of biofilms arises in many different environments and on many differing environments, including treatment of water supplies, treatment of medical and dental equipment, treatment during medical and dental procedures, and general cleaning and disinfecting of a wide range of surfaces. Even though there is a wide range of areas for which treatment may be necessary or desirous, there are also some common factors to take into account. Treatment compounds and solutions must not be too corrosive for their intended uses. For example, you would not use an overly strong solution, as this may etch and damage a surface, or cause pain and injury if used during medical or dental procedures. Thus, it is necessary to provide solutions that are strong enough to treat biofilms without causing irreversible damage.

There have been several ways discussed to treat biofilms, such as processes using halogen and oxygen based compounds, including hypochlorite, chlorite, chlorate, and peroxygen compounds, to treat biofilms. However, especially when treating biofilms related to people and internal surfaces, such as on the dentin of teeth during procedures like root canals, care must be taken so that the treatment process is not dangerous to an individual. Furthermore, treatment of a mature biofilm is often unsuccessful because the biocides only react with the outer layers of the biofilm and tend not to sufficiently treat the entire surface areas, external and internal, leaving a healthy and substantial bacterial community on the surface of the substrate, which rapidly regrows. Bacteria within biofilms also develop increasing resistance to biocides on repeated dosing. It has been found that biocides further induce cross-resistance to other biocides.

A range of bactericidal substances, commonly termed biocides, germicides, or microbicides, are available, all of which are claimed by their producers to quantitatively to kill bacteria occurring in aqueous systems. Biocides target a range of cellular loci, from the cytoplasmic membrane to respiratory functions, enzymes and the genetic material. However, different bacteria react differently to bactericides, either due to inherent differences such as unique cell envelope composition and non-susceptible proteins, or to the development of resistance, either by adaptation or by genetic exchange. Bactericides should therefore be evaluated against the organisms which they are chosen to control, i.e. the dominant ones in the system to be treated. The composition of microbial populations in systems varies with the environment, and changes considerably after treatment with various biocides by selection for resistant strains. Bacteria growing as biofilms are also significantly more resistant to most of the currently known antimicrobial agents, as compared to planktonic bacteria, posing ongoing challenges for methods for their control.

In treatment for medical and dental situations, a few solutions have been developed that are currently used. Examples of compounds commonly used in medical treatments include quaternary ammonium compounds, parachlorometaxylenol compounds, gluteraldehyde compounds, phenolic compounds, such as chlorophenols, phenols, and thymol, peroxyacetic aced, alcohols, chlorine dioxide, chloroxyenols, tetracyclines, iodine, cresols, caprylic acid, formaldehyde, and trichlorosan compounds. While useful, there are still drawbacks. These compounds can have adverse side effects and possible negative impacts if used too often or in too great of concentrations. Other examples include highly corrosive materials, such as sodium hypochlorite, calcium hypochlorite, or other hypochlorite or hypohalogen compounds. Consequently, only small amounts of these materials can be safely used on and around humans. However, these compounds also tend to oxidize rather quickly, which reduces the efficacy of these compounds over time. Once these compounds are opened and come into contact with the air, the shelf life for these products is relatively short due to decomposition of the compounds. To correct for this shortcoming, the strength of these compounds ideally would be high. However, as stated above, it is not possible to make the products too strong, or they could do severe damage to a patient.

The prior art does not adequately provide a stable agent that maintains acceptable stability after storage times and storage conditions typical of actual usage conditions encountered in the real world. For instance, most commercial product distribution channels result in products aging several months following manufacture before being placed on sale, followed by significant delays before actually being used. During this time, products are seldom stored under ideal conditions, but rather are exposed to temperature variations typical of the home, field and industrial environment.

Many typical commercially sold bleach products containing hypochlorite solutions have a half-life of around six months or less. This stability is generally sufficient for everyday household cleaning chores and duties. In medical and dental situations better stability is desired, especially when other compounds are added to the hypochlorite solutions. When wetting agents, surfactants, penetrating agents, and/or other similar additives and active agents are added to the hypochlorite solutions, stability and efficacy is lost due to oxidation of the agents.

Other treatment solutions and detergent compositions in the medical and dental field are known in the art. Chlorhexidine based compounds are one class of compounds used in biocide solutions and antimicrobial solutions.

Chlorhexidine is used to prevent and treat the redness, swelling, and bleeding of the gums associated with gingivitis. It is classified as a biguanide antimicrobial drug. Chlorhexidine is generally accepted to be effective as an antiseptic hand wash for methicillin-resistant *Staphylococcus aureus* (MRSA). Chlorhexidine is obviously an easily tolerated and effective antiseptic for the daily practice of medicine and surgery. Its oral use is also well documented (e.g. in ill subjects who cannot brush their teeth adequately). However, the teeth discolorations that are caused by the drug are disturbing.

Chlorhexidine is an antiseptic agent effective against plaque, oral flora including *Candida* sp. And *Candida albicans*, and is used as a cleanser for surgical scrub 1 skin wounds 1 germicidal hand rinse, and as an antibacterial dental rinse. Chlorhexidine is active against gram-positive and gram-negative organisms, facultative anaerobes, aerobes, and yeast. Chlorhexidine is essentially nontoxic when applied to the skin or mucous membranes/compared with disinfectants including cresol, bleaching powder, and phenol which are, in general, toxic to cells of the body. Other common antiseptic agents include benzalkonium chloride, cetrimide, hexachlorophene, iodine compounds, mercury compounds (i.e. thimerosal), alcohol and hydrogen peroxide, hexamine hippurate, triclosan, cetylpyridinium, chloride, and dequalinium. Other substances which can be used for antiseptic purpose include boric acid and volatile oils such as methyl salicylate and some botanical essential oils.

Hexachlorophene and benzalkonium chloride are used primarily in hand or face washes. Benzalkonium chloride must not be applied to areas which have not been fully rinsed as it is inactivated by organic compounds. Benzalkonium application may include disinfecting instruments and preserving drugs in low concentration form. Aqueous iodine solutions are less effective than alcoholic solutions, but the drying effect of the alcoholic component can be irritating to abraded skin. Povidone iodine is convenient to use as it is less irritating, but not as effective.

Chlorhexidine is also used as a safe antiseptic or disinfectant application to prevent body infection and in oral rinses for treating sore gums, mouth ulcers, periodontal and endodontic infections, and preventing plaque on teeth. It is used in the form of acetate, gluconate or hydrochloride, either alone or in combination with other compounds, such as cetrimide. However, these chlorhexidine compounds have a tendency to gel or coagulate when agents, such as surfactants, wetting agents, leveling agents, penetrating agents and the like, are added to the compounds. To prevent clotting or gelling, processes, which may include intricate steps, are carried out so that the compound has a suitable and useful equilibrium. However, in forming a stable solution or compound some of the efficacy of the system may be lost.

Thus, it would be advantageous to develop compounds and systems for medical, dental, and general cleaning solutions that have increased stability without overly affecting the efficacy of the solution.

SUMMARY OF THE INVENTION

The present invention is directed towards irrigation and disinfection solutions. The solutions comprise disinfectants combined with surfactants or surface agents, wherein the surfactants are capable of complexing with one another. The result is disinfectant solutions having synergistic effects.

The solutions have enhanced properties that were previously not attainable in the art, such as enhanced leveling, wettability, suspension, and emulsification, among other properties. Furthermore, the solutions have improved stability compared to the industry standard solutions, which was an unexpected result. Since the solutions are more stable, the efficacy of the solutions are more consistent over extended periods of time compared to the standard solutions previously used in the art, which leads to a better shelf life than those solutions. This can lead to an economically advantageous solution, as potentially less solution is needed for a procedure compared to previous solutions.

Generally, the solutions are comprised of a disinfectant in combination with a basic or polar solvent compound. The solutions further comprise at least one surfactant, and preferably two or more surfactants.

The present invention also comprises a dental irrigant that has improved efficacy features and qualities compared to the prior art, while also being a sufficiently stable product. The irrigant comprises an aqueous solution containing a disinfectant, such as sodium, calcium, potassium, or lithium hypochlorite (NaOCl, CaOCl, KOCl, LiOCl) and similar hypochlorite compounds in combination with a strong base, such as a hydroxide compound. The composition further includes surfactants that contain ethoxylates, more specifically alkylphenolethoxylates and alcoholethoxylates. The compositions have improved performance qualities over the prior art. For instance, compared to currently used wetting agents, the solution of the current compositions have improved wetting and leveling qualities, and also improved penetration and digestibility, and breaks down biofilms more efficiently. The solution also has a longer shelf life compared to the prior art, which results in the solution having a more consistent potency after the solution comes into contact with air. The composition comprises approximately up to 8% of the hypochlorite compound, up to about 2% of the basic compound, and up to about 2% of the ethoxylate compound. Other surfactants may be present in the irrigant.

The present invention further provides an improved method of irrigating dental surfaces, such as root canals and the like. With the use of the improved surface treatment agent or surfactants, wetting agent, penetrating agents, or leveling agents of the present invention, it is possible to more efficiently treat and clean dental cavities, such as root pulp canals and caries. These surface agents also are referred to as surface modifiers.

The present invention also contemplates the use of stable chlorhexidine solutions that can be used for a wide variety of situations, including medical and dental uses, general cleaning and antiseptic uses, treating and disinfecting of water lines, and used in commercial products, such as sprays and wipes. The solutions and products generally comprise at least a tertiary compound, which will be discussed in further detail.

The solutions can also be used as an improved disinfectant, in general, and for specific purposes, such as disinfecting and cleaning water lines. These and other improvements will become more evident with the detailed description below.

DESCRIPTION OF THE PREFERRED EMBODIMENT

Although the disclosure hereof is detailed and exact to enable those skilled in the art to practice the invention, the physical embodiments herein disclosed merely exemplify the invention which may be embodied in other specific structures. While the preferred embodiment has been described, the details may be changed without departing from the invention, which is defined by the claims.

Disinfectant and irrigant solutions according to a first embodiment of the present invention generally comprise three separate compounds or compound groups: (1) a disinfectant, preferably a hypohalogen salt, such as a hypochlorite compound; (2) a strong alkali or basic compound, such as sodium hydroxide (NaOH) or potassium hydroxide (KOH); and (3) a surfactant compound or compounds. A strong basic compound is a substance which completely hyrdolyzes and disassociates in an aqueous system and raises the pH of water from about 7.0 to 14.0. The surfactants, also called surface agents, generally are selected from ethoxylates, fluorosurfactants, sulfonate surfactants, polyglucosides, amine oxides, and other similar compounds known and used in the art. The surfactants are provided in the solution in a manner that they will complex with one another, thereby providing synergistic effects for the solution overall.

Table 1 provides a breakdown of one possible first embodiment of a composition for the treatment solution of the present invention. The solution is an aqueous based solution. The percentages given are weight percentages. However, it is understood that other percentages and ranges may be used and fall within the scope of the present invention. Likewise, other surfactants may be incorporated into the solution, or may replace one of the listed surfactants. As an example, it is possible to replaced the phenolethoxylate surfactant listed in Table 1 with a different surfactant, such as an ammonyx-LO (N,N-dimethyldodecylamine-N-oxide) surfactant, and the solution would still fall within the scope of the present invention.

TABLE 1

| Component | Weight Percentage of Overall Composition |
| --- | --- |
| Water | 99.5%-83.0% |
| Sodium Hypochlorite (NaOCl) | 0.01%-10.0% |
| Sodium hydroxide (NaOH) | 0.01%-2.0% |
| Commercial grade phenolethoxylate surfactant | 0.01%-2.0% |
| Sulfonate surfactant | 0.01%-5.0% |
| fluorosurfactant | 0.01%-2.0% |

The main active ingredient of the solution as shown in Table 1 is a hypohalogen compound. Possible solutions include sodium, lithium, calcium, or potassium hypochlorite solutions, or generally alkali or alkaline earth metal hypohalogen compounds, such as hypobrimide, as is known and understood by the art. One source for the chlorite compound comes from bleach, such as Clorox® bleach, manufactured by The Clorox Company. As an example, a sodium hypochlorite test solution containing 6% sodium hypochlorite was found adequate to perform in accordance with the present invention. The hypochlorite compound preferably has a pH in the range of 10.50-13.50.

A strong basic compound, such as sodium hydroxide (NaOH) or potassium hydroxide (KOH), is also present in the solution. In the example depicted in Table 1, sodium hydroxide (NaOH) is present in the compound or solution, with between 0.01% and 2% of the weight of the solution, with the NaOH either being introduced as an aqueous solution or in powder form.

In a preferred embodiment of the solution, the solution further comprises an ethoxylate compound, such as octylphenol ethoxylate or nonophenol ethoxylate. Approximately 0.01%-2.0% of the phenol ethoxylate will 15 be used in the present invention. Preferred ethoxylate compounds include alkyl phenol ethoxylates, phenol ethoxylates, alcohol ethoxylates, also called synthetic or fatty alcohol, and related or similar compounds and combinations thereof. Below is a general formula for octylphenol ethoxylate:

R = octyl (C8) x = 9.5 (avg)

R in the above formula preferably is a carbon chain between $C_8$ and $C_{16}$. Similar commercial solutions, such as Triton™ X-100 Surfactant and TRITON™ CG-110 Surfactant, both produced and sold by the Dow Chemical Company ("Dow"), are manufactured, with the "X" generally indicating the number of moles of the ethoxylate or alcohol ethoxylate in the product or solution. Triton™ X-100 contains approximately 100 moles of alcohol ethoxylate. TRITON™ CG-110 contains approximately 110 moles of an alkyl polyglucoside compound. In the solution according to the present invention, approximately 3-15 moles of the noted there are ethoxylate compounds present, with a more preferred amount being around 9-11 moles.

Another possible ethoxylate surfactant is TERGITOL™ 15-S-7, also purchased from Dow, which is a secondary alcohol ethoxylate nonionic surfactant. TERGITOL™ 15-S-7 is soluble in water, soluble in chlorinated solvents and most polar organic solvents. It is also stable in the presence of dilute acids, bases, and salts, and is compatible with anionic, cationic, and other nonionic surfactants.

The solution further comprises another surfactant, preferably a sulfonate surfactant, comprising approximately 0.01%-5.0% of the weight of the solution. The preferred surfactant is soluble in water and highly soluble in strong acid and alkali solutions. A mixture of decyl benzene sulfonic acid or benzene sulfonic acid with a disodium salt would be such a surfactant. Generally, diphenol sulfonates, alkyl aryl sulfonates, aryl sulfonates, alkyl sulfonates, both branched and unbranched, and diaryl sulfonates, and combinations thereof are acceptable as surfactant. One example of such a surfactant is alkyldiphenyloxide disulfonate, sold as Dowfax C10L by Dow. However, other compounds may also be included, such as amine oxides having a general formula of:

Where $R_1$, $R_2$, and $R_3$ are preferably carbon chains between $C_8$ and $C_{18}$, and more preferably carbon chains between $C_{10}$ and $C_{14}$.

The preferred embodiment of the solution also includes a fluorosurfactant, comprising approximately 0.01%-2% of the solution. Preferred surfactants are fluorotelomer of fluoroligomer monoethers, usually arranged with a polyethylene glycol (PEG) compound. These ethoxylated nonionic fluorosurfactants give exceptional low aqueous surface tensions at concentrations as low as 0.002% (20 ppm). This type of fluorotelomer has a general structure of:

Where Rf=F $(CF_2CF_2)$ y

X=0 to about 15

Y=1 to about 7

An example of a fluorosurfactant is DuPont™ Zonyl® FSO, a fluoroalkyl alcohol substituted monoether combined with polyethylene glycol, which is produced and manufactured by the DuPont Company. The compound is an ethoxylated nonionic fluorosurfactant that is generally considered to have effective emulsifying and dispersing qualities and highly effective wetting qualities.

The overall solution has a pH within the range 30 of 10.5 to 13.5. It should be noted that the above values are exemplary and that each of the specific compounds can fall within a certain range. For instance, NaOCl could be within the range of 0.02% to 8.0%. Additionally, alternate chlorite compounds may be used, including alkali earth metal and/or alkaline earth metal hypohalogens selected from the group consisting of sodium hypochlorite, potassium hypochlorite, magnesium hypochlorite, lithium hypochlorite, calcium hypochlorite, and mixtures thereof.

Similarly, other strong basic compounds could be used instead of NaOH, including other alkalines, i.e. KOH, MgOH, LiOH, CaOH and mixtures thereof. The amount of the hydroxide can range from 0.02 to 2.00%.

As stated above, different ethoxylates, preferably alkyl phenol ethoxylates, are present in the current invention, having an approximate range of between 3 and 18 moles of ethylene oxide.

The present invention can incorporate a wide range of surfactants, including anionic, cationic, and nonionic surfactants, and potentially amphoteric, and zwitterionic surfactants. As noted above, surfactants and surface agents of particular interest are fluorinated telomers and derivatives thereof.

The present invention also provides another improved wetting, leveling, and/or penetrating compound or solution. In this embodiment, the solution comprises a chlorhexidine compound, preferably a chlrohexidine gluconate compound, with a sugar ester surfactant. One such surfactant is Tween® 80. Tween® 80 (Polysorbate 80) is a hydrophilic nonionic surfactant commonly used as an ingredient in dosing vehicles for pre-clinical in vivo studies (e.g., pharmacokinetic studies, etc.) It is derived from polyoxylated sorbitol and oleic acid, and is a viscous, water-soluble yellow liquid. The hydrophilic groups in this compound are polyethers also known as polyoxyethylene groups which are polymers of ethylene oxide. In the nomenclature of polysorbates, the numeral designation following polysorbate refers to the lipophilic group, in this case the oleic acid. However, as noted earlier, the surfactant tends to gel when introduced into a chlorhexidine compound. Thus, prior art did not allow a combination of the compounds in effective, useful amounts. Similarly, other surfactants, such as flourotelomers, were not easily and usefully introduced into such a solution, as they also immediately reacted with the chlorhexidine.

The present invention addresses this problem by introducing a tertiary surfactant system. The surfactants include sugar ester surfactants, glucoside surfactant, including alkyl glucosides and similar glucosides, and fluorinated surfactants, similar to the surfactants discussed in the prior embodiment of the invention. The present solutions provide blended solutions made by combining individual solutions, which consist of diluted amounts of the various surfactants.

Thus, a first solution is prepared with the sugar ester. As an example, an aqueous solution containing approximately 12% Tween 80 by weight was prepared. A second aqueous solution was prepared containing approximately 20% by weight of an alkyl glucoside compound. Finally, a third aqueous solution containing approximately 2% by weight of a fluorotelomer was prepared.

These solutions were combined together in another final aqueous solution, preferably in equal amounts, preferably with each solution comprising approximately 1% by weight of the total solution. The final solution contained a chlorohexidine compound, such as chlorhexidine gluconate compound, which comprised approximately 10% of the solution. The final solution maintained bioefficacy and stability for the solution, had stable wetting, leveling, and penetrating qualities, and also maintained sufficient conductivity. Furthermore, the solution did not clot or gel as would have been expected from the prior art.

The amounts given are just examples and should not be considered as limiting the ranges at which the solution properly performs. Provided that a chlorhexidine compound can be combined with various surfactants to provide a usable solution that will not unduly clot or gel and will retain sufficient beneficial properties, the compound would fall within the scope of the present invention.

For example, it has been determined according to the present invention that chlorhexidine compounds can be combined with other chelating agents or compounds to form stable solutions. One example is a combination of a chlorhexidine gluconate compound (CHG) with ethylenediaminetetracetic acid, commonly referred to as EDTA. Generally, mixing CHG with EDTA formed a white precipitate or flocuculant. Other combinations include CHG with citric acid. Preferred embodiments of these solutions are shown below in Table 1A. The individual compounds are listed as a percentage of the overall solutions.

TABLE 1A

Chlorhexidine Solutions

| Compound | CHG with EDTA | CHG with citric acid |
|---|---|---|
| CHG | 3.00% | 10.00% |
| EDTA | 1.00% | NA |
| Citric Acid | NA | 2.00% |
| Triton CG-110 | 3.04% | 2.00% |
| Zonyl FSO (aqueous solution) | 2.0% | NA |
| $H_2O$ | 90.16% | 83.00% |
| Tergitiol 15-S-7 | NA | 2.00% |
| Ammonium hydroxide | 2.20% | NA |

As with the other discussed solutions, the listed values are merely exemplary and other ranges of compounds and surfactants will fall within the scope of the present invention. Provided that a chelating compound or solution allows for the added surfactants to complex with one another, and with the chelating agent or the chlorhexidine compound, the resultant solution will fall within the scope of the present invention.

The present solutions are also believed to have potentially improved qualities when an electrical current is introduced together with the solution. When the charge is applied, negative ions of an antimicrobial agent may be encouraged to diffuse toward an applied positive pole, which may help the present solutions to penetrate into small tubules and crevices. Electrical stimulation is also known to make biofilms more susceptible to chemical disruption. Furthermore, with the high conductivity of hypochlorite based solutions combined with an electrical current allows for more rapid debridement of organic material compared to the prior art. It is also believed that the present invention and solutions will have improved qualities when treated with other mediums, such as heat and light. As an example, it may be possible to introduce the solutions, specifically the chlorhexidine gluconate solution, to an iontophoretic process to further increase the efficacy of the solution.

The solution has other improvements over the prior art. The solution also can be used for a wide range of uses, such as general cleaning and disinfecting, sterilizing of medical and dental equipment, and cleaning of fluid lines. The solutions can also be incorporated into cleaning supplies, such as disinfectant wipes. The improved stability and consistent strength of the solution will provide cost savings compared to prior art solutions. That is, because the solutions will retain a longer stability than prior art and be efficacious over a longer time compared to the prior art, less amount of the solution will be used. Thus, even if the cost to make the solutions is higher than current solutions used, the amount of solution used for a specific task will be smaller than the prior art amount, which will lead to lower costs overall.

Sample Solutions

Batch solutions were produced in accordance with the above criteria and were compared to current products and standards of the industry. Solutions can be prepared as follows:

Example 1

Figure 1:
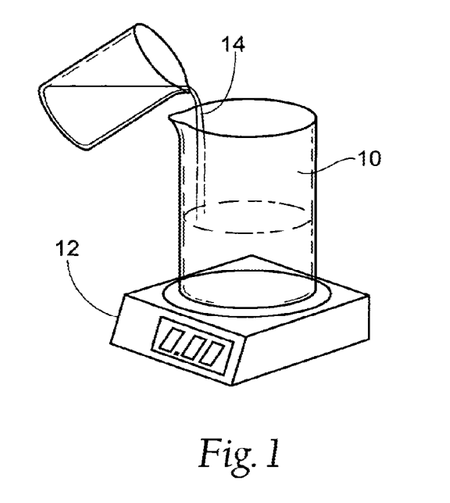
FIGS. 1-9 demonstrate a first method for mixing a solution in accordance with the present invention.

FIGS. 1-9 demonstrate a procedure for mixing a first solution according to the present invention. In FIG. 1, the solution is initially prepared by placing a first beaker 10 on a scale 12. The scale 12 is tared to zero and the first beaker 10 is filled with 157.4±0.1 g of a first surfactant 14, preferably Tergitol 15-S-7, and then set aside. A pipette or syringe may be used if necessary to get an accurate amount of the first surfactant.

Figure 2:
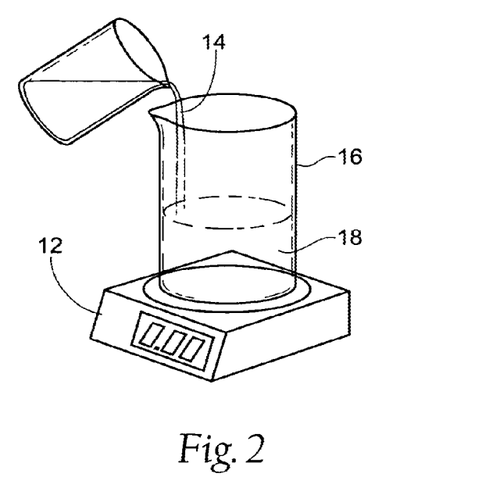

In FIG. 2, a second beaker 16 is placed on the scale 12, and the scale 12 is tared to zero. The second beaker 16 is filled with 435.8±0.1 g of a second surfactant 18, preferably Triton CG-110, and then set aside. As noted with the first surfactant 14, a pipette or syringe may be used for measuring an accurate amount of the surfactant 18.

Figure 3:
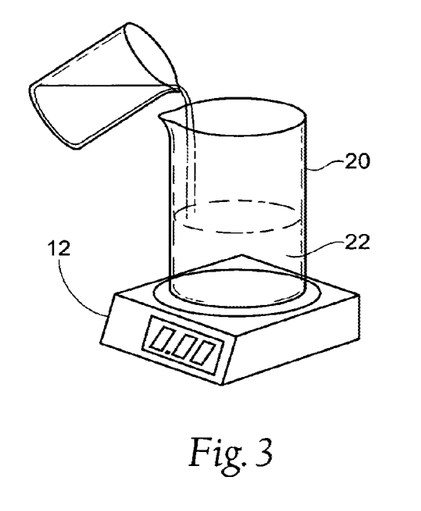

FIG. 3 shows a third beaker 20 placed on the scale 12, and the scale 12 is tared to zero. The third beaker 20 is filled with 858.7±0.1 g of a third surfactant 22. As an example, an aqueous solution containing 2.5% of a fluorosurfactant could comprise the third surfactant 22. Similar to the measurement of the previous surfactants, a pipette or syringe may be used for measuring an accurate amount of the surfactant 22.

Figure 4:
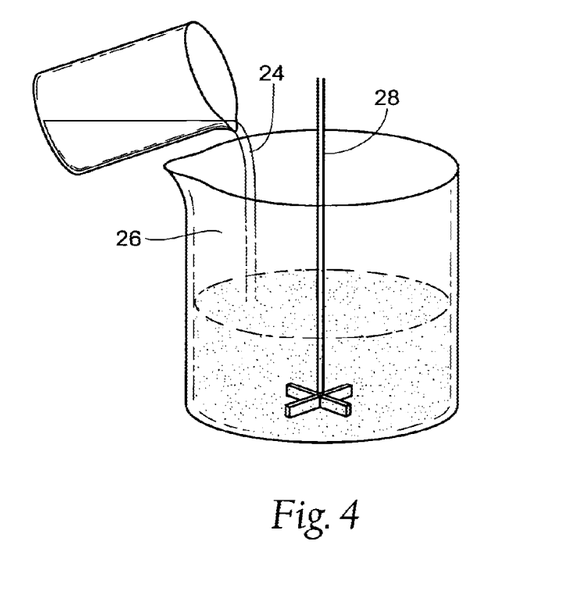

In FIG. 4, distilled water 24 is added to a large mixing tank 26. The tank 26 is preferably a Nalgene cylindrical tank, but any tank having a sufficient volume may be used. Twenty (20) gallons of water 24 is added to the tank. A mixer 28 is inserted into the tank to 26 provide agitation. The mixer 28, which can be any mixer known and used in the industry, such as the mixers produced by The Barnant Company, is started, thereby agitating the water 24.

Figure 5:
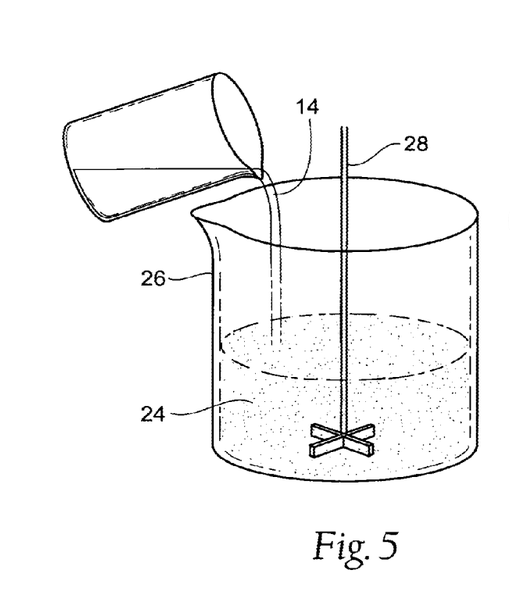

FIG. 5 demonstrates that the first surfactant 14 is slowly added to the distilled water 24 in the tank 26, and the solution is further agitated for approximately one (1) minute.

Figure 6:
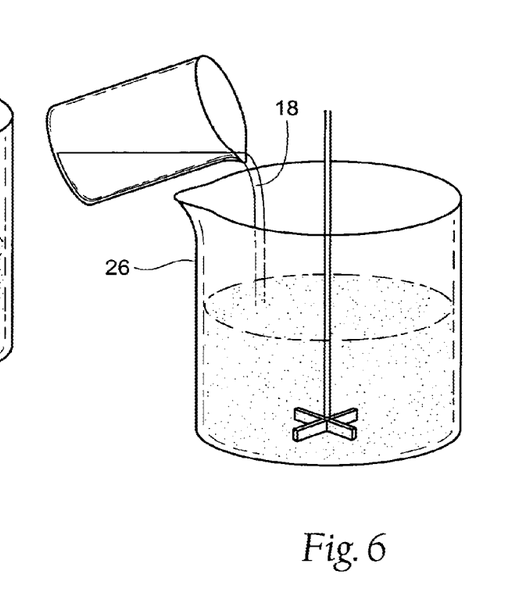

In FIG. 6, the second surfactant 18 is slowly added to the mixture of FIG. 5, and is further agitated one (1) minute.

Figure 7:
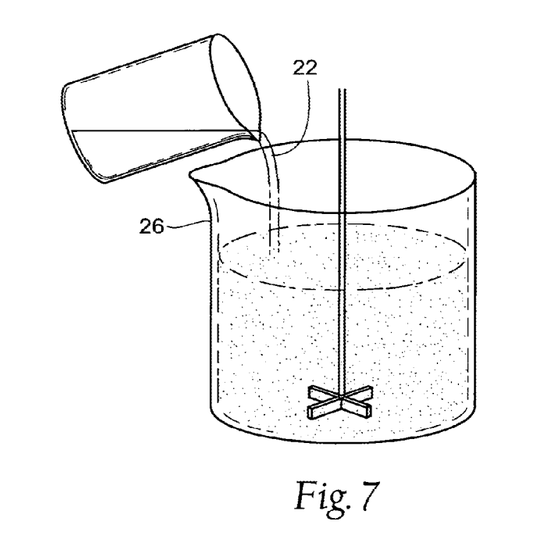

In FIG. 7, the third surfactant 22 is slowly 20 added to the mixture of FIG. 6 and allowed to agitate.

Figure 8:
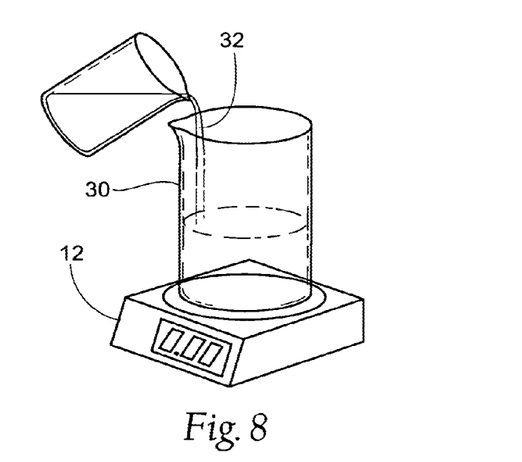

While the mixture agitates, a container 30, possibly a plastic pitcher, is placed on the scale 12 and tared to zero, as is demonstrated by FIG. 8. The container 20 is filled with an aqueous chlorhexidine solution 32. One such solution is an aqueous solution containing chlorhexidine gluconate (20% w/v). 8580±0.1 g of the chlorhexidine solution 32 is weighed out and added to the tank 26. The mixture is further agitated for one (1) minute.

Figure 9:
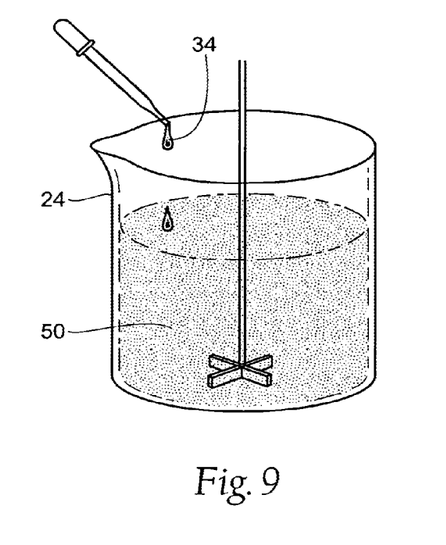

Finally, as demonstrated in FIG. 9, a dye 34 can be added to the tank 24, if desired. A small amount of dye 34 is sufficient to provide coloring for the mixture. In the present example, an aqueous dye solution comprising methylene blue chloride (1% w/v), approximately 40 g of the dye solution, is added to the mixture. Agitation continues, approximately twenty minutes, until the dye 34 thoroughly dissipates through the mixture, though other mixing times may be used. The final solution 50 was tested and the results are listed, as follows.

Results

Various solutions were prepared similarly to the above procedure, which includes a chlorhexidine compound according to the present invention. These solutions were tested for various qualities, such as pH, surface tension, conductivity, specific gravity, and the color of the solutions. Generally, the tests were carried out between about 75° and 78° F. These solutions were tested against the current industry standards and are listed below in Table 2.

TABLE 2

Solutions Containing Chlorhexidine Compounds

| Characteristic | Test Solution 1 | Test Solution 2 | Current Standard |
|---|---|---|---|
| pH | 5.64 | 5.64 | 5.62 |
| Surface Tension | 26 dynes/cm | 26.3 dynes/cm | 47 dynes/cm |
| Conductivity | 1590 mSm/cm | 1585 mSm/cm | 1522 mSm/cm |
| Specific Gravity | 1.038 grams/cm$^3$ | 1.037 grams/cm$^3$ | 1.040 grams/cm$^3$ |
| Color (human observation) | Same as standard | Same as standard | NA |

The results showed that the solution generally met or exceeded current industry standards. The surface tension was significantly decreased, which leads to improved leveling and wettability qualities.

Freeze Thaw Cycle—Stability Studies:

The above Test Solutions were tested to determine the stability of the solutions. Each of the solutions 5 was tested three times, with the value averaged for each solution. Open weighing dishes were used to freeze the solutions. The weighing dishes were made of Pyrex glass, having a diameter of 8 cm and a depth of 2.5 cm. 50 grams of each solution were frozen and then thawed, with the results given below.

Results:

1) The solutions were within the limits of acceptable stability for dental solutions. That is, the test solutions indicate that they would meet the required properties for standard irrigants currently in use in the related dental and medical fields.

Hypochlorite solutions prepared similar to the above procedure were further tested for stability.

Example 2

Figure 10:
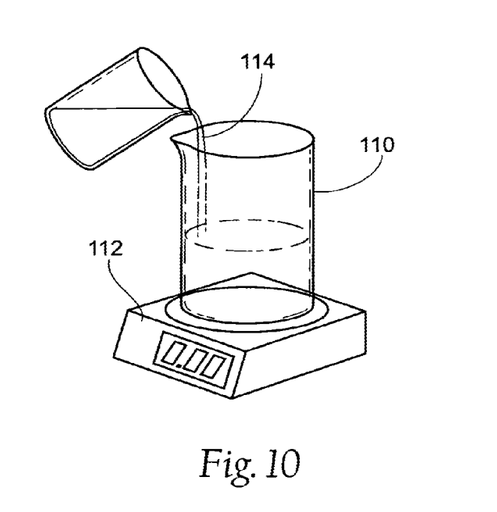
FIGS. 10-18 demonstrate a second method for mixing a solution in accordance with the present invention.

FIGS. 10-18 demonstrate the preparation of a second test solution prepared according to the present invention. In FIG. 10, a first beaker 110 is placed on a scale 112. The scale 112 is tared to zero and the first beaker 110 is filled with a basic solution 114, such as an aqueous sodium hydroxide solution (50% w/v), and then set aside. A pipette or syringe may be used if necessary to get an accurate amount of the basic solution 114. Preferably 93.0±0.1 g of the basic solution 114 is measured.

Figure 11:
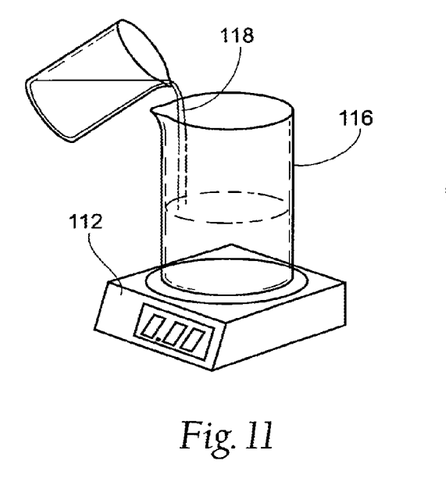

FIG. 11 shows a second beaker 116 being placed on the scale 112, and the scale 112 is tared to zero. The second beaker 116 is filled with 92.8±0.1 g a first surfactant 118, preferably Dowfax C10L, and then set aside. As noted with the basic solution 114, a pipette or syringe may be used for measuring an accurate amount of the first surfactant 118.

Figure 12:
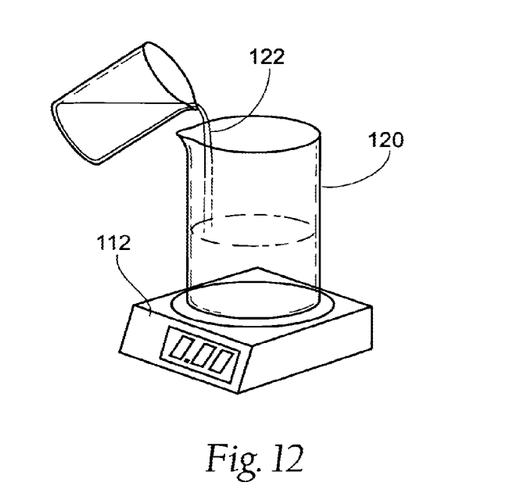

FIG. 12 shows a third beaker 120 being placed on the scale 112, and the scale 112 is tared to zero. The second beaker is filled with 97.0±0.1 g of a second surfactant 122, preferably Triton X-100, and then set aside. As noted with the previous compounds, a pipette or syringe may be used for measuring an accurate amount of the second surfactant 122.

Figure 13:
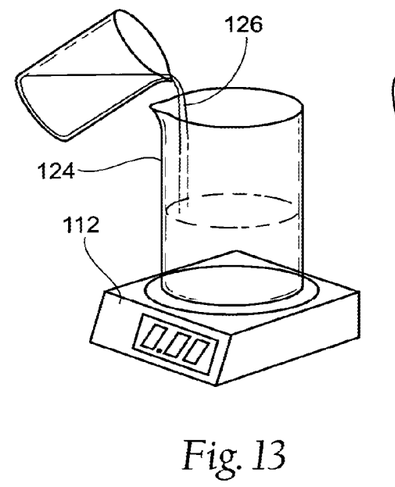

FIG. 13 shows a fourth beaker 124 being placed on the scale 112, and the scale 112 is tared to zero. The fourth beaker 124 is filled with 184.1±0.1 g of a third surfactant 126. As an example, an aqueous solution containing 2.5% of a fluorosurfactant may comprise the third surfactant 126. Similar with the previous surfactants, a pipette or syringe may be used for measuring an accurate amount of the surfactant 126.

Figure 14:
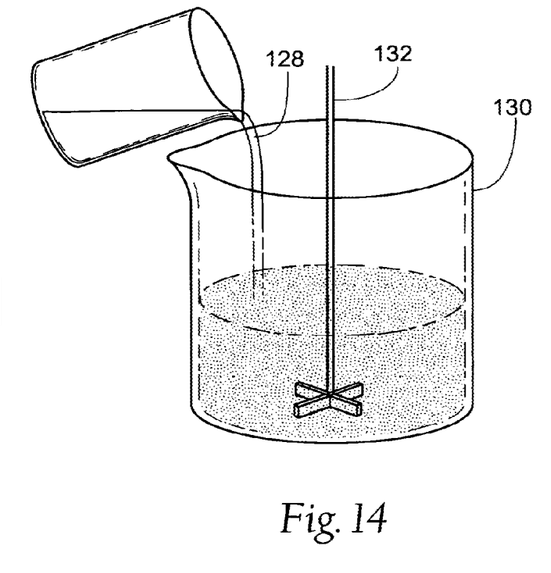

In FIG. 14, a hypochlorite solution 128 is added to a large mixing tank 130. The tank 130 is preferably a Nalgene cylindrical tank, but any tank having a sufficient volume may be used. Approximately 4¼ gallons of hypochlorite solution 128 is added to the 25 tank, such as 4¼ gallons of commercially sold Clorox® bleach. A mixer 132 is inserted into the tank 130 to provide agitation. The mixer 132, which can be any mixer known and used in the industry, such as the mixers produced by The Barnant Company, is started, thereby agitating the hypochlorite solution 128.

Figure 15:
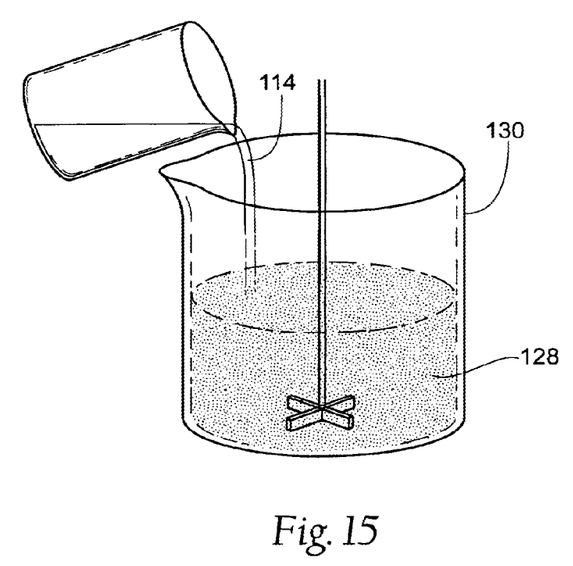

In FIG. 15, the basic solution 114 is slowly added to the hypochlorite solution 128 and the solution is further agitated for approximately one (1) minute.

Figures 16, 17, 18:
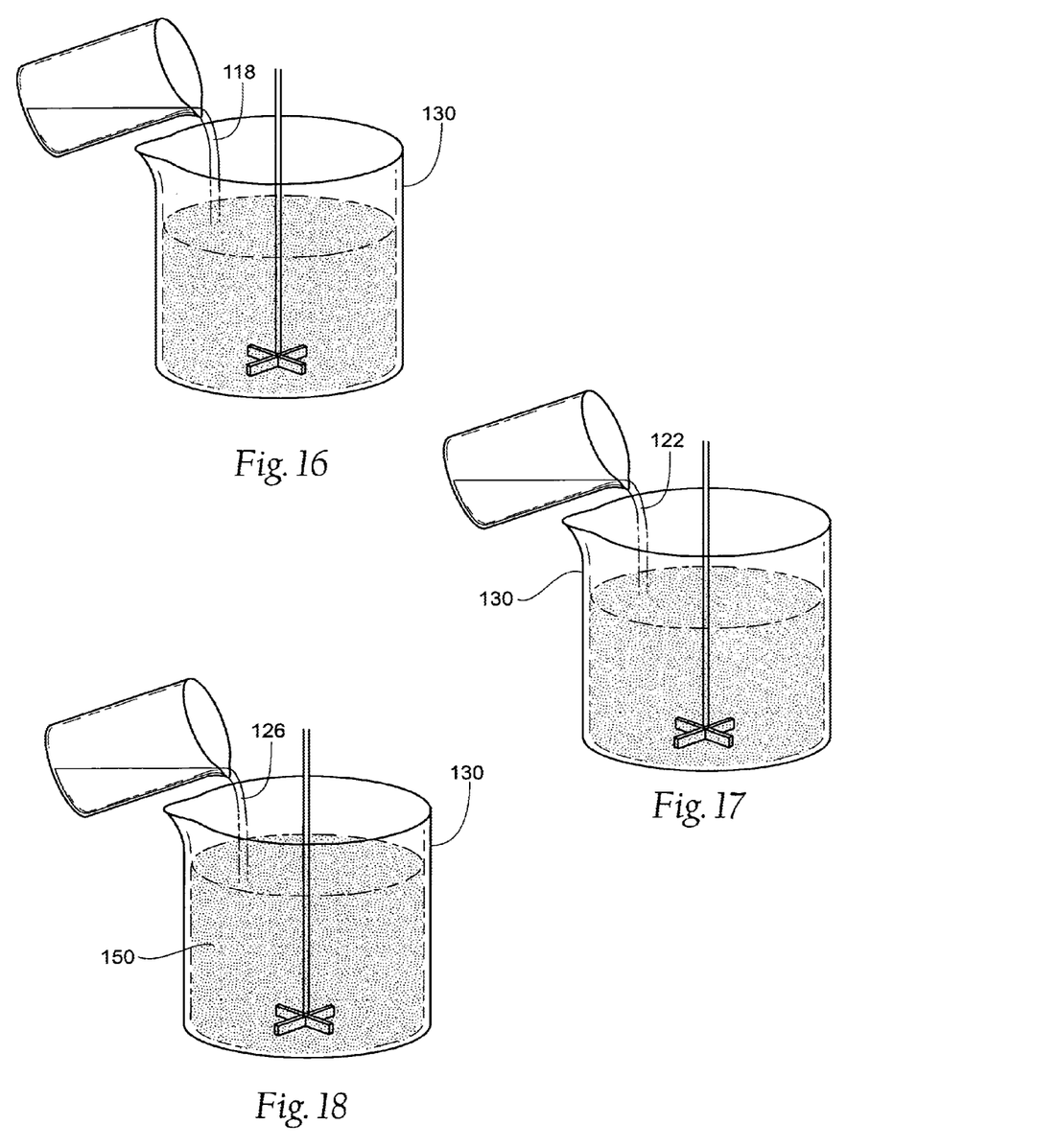

In FIG. 16, the first surfactant 118 is slowly added to the mixture of FIG. 15 and is further agitated one (1) minute.

In FIG. 17, the second surfactant 122 is slowly added to the mixture of FIG. 16 and allowed to agitate.

Finally, in FIG. 18 the third surfactant 126 is slowly added to the mixture of FIG. 17, and is further agitated for twenty minutes so that all the individual compounds are thoroughly mixed, but other mixing times are possible. The final solution 150 was tested and the results are listed, as follows.

Various solutions prepared according to the second procedure, which includes a hypochlorite compound, were tested for various qualities, such as pH, surface tension, conductivity, specific gravity, and the color of the solutions. Generally, the tests were carried out between about 75° and 78° F. These results are listed below in Table 3.

TABLE 3

Solutions Containing Hypochlorite Compounds

| Quality | Test Solution 1 | Test Solution 2 | Test Solution 3 | Test Solution 4* | Test Solution 5 |
|---|---|---|---|---|---|
| pH | 12.38-12.46 | 12.48 | 12.38 | 12.49-12.51 | 12.41 |
| Surface Tension | 29.82-31.7 dynes/cm | ~29 dynes/cm | 30.41 dynes/cm | 29.82-31.7 dynes/cm | 30.2 dynes/cm |
| Specific Gravity | 1.108 g/cm$^3$ | 1.113 g/cm$^3$ | 1.108 g/cm$^3$ | 1.104 g/cm$^3$ | 1.106 cm$^3$ |
| Conductivity | 128.3-132.9 mSm/cm | ~130 mSm/cm | 131.2 mSm/cm | 131.2 Sm/cm | 130.2 mSm/cm |
| Available Chlorine | 5.82%-6.01% (v/v) | 6.05% (v/v) | 5.84% (v/v) | 5.82%-5.87% (v/v) | 5.95% (v/v) |
| Color | Clear light straw color, no visible particles | Aqua clear to light straw color, no visible particles | Aqua clear to light straw color, no visible particles | Clear light straw color, no visible particles | Clear light straw color, no visible particles |

*Test Solution 4 included three separate solutions, with the range of results given.

The results were consistent with the characteristics of current solutions in the art. Further, the surface tension and available chlorine showed improved qualities over the prior art. The color of the solutions matched the standards in the art, with the color tested by using an HP model 8453 UV-VIS spectrophotometer. Solutions prepared similar to the second procedure were further tested to determine stability of the solutions, using a freeze thaw method, similar to the method used, above.

Freeze Thaw Cycle—Stability Studies:

Hypochlorite solutions prepared according to the present invention were tested against a standard industry disinfectant, a Clorox® bleach product produced by The Clorox Company. Both solutions contained sodium hypochlorite. The test was carried out as follows:

Three sixty gram samples of a hypochlorite solution and three sixty gram samples of the Clorox® product were poured into separate two (2) ounce glass bottles. The samples were frozen and then thawed. The average results are given below.

Results:

The solutions prepared according to the present invention had no visible particles or suspended solids once the solutions were thawed. The Clorox® product had visible suspended particles upon thawing and, also, had a visible heavy haze. This indicates that the solutions according to the present invention have comparatively better stability.

After three inversions after thawing, striation disappeared in the solutions according to the present invention. The Clorox® product required six inversions after thawing for the striation to disappear.

Striation is the visible separation of the different compounds within a solution that is commonly scene after a solution is frozen. Inversion is flipping the container containing the solution and then uprighting the container, to provide for the striated compounds to remix with one another. The results demonstrate that the solution according to the present invention show improved stability according to known solutions, as they remix quicker than the known solutions.

The pH for the solutions according to the present invention did not change after thawing. The Clorox® product had a pH drop of 0.25 from 12.85 to 12.60 after thawing. This also shows that the present invention has improved stability compared to the industry standard.

Comparative Examples

The following comparative examples were used to compare the properties of solutions according to the present invention to standard solutions in the industry.

Comparative Examples 1 and 2 are based on the present invention and Comparative Examples 3 and 4 are standard solutions of the industry.

Comparative Example 1

Bleach [6% Sodium Hypochlorite (NaOCl)]: 97.50%
Sodium Hydroxide (50%): 02.00%
Dowfax C-10L (anionic detergent): 00.15%
Triton X-100 (nonionic detergent): 00.20%
Fluorosurfactant (2.5%): 00.15%

Comparative Example 2

Distilled Water: 95.97%
Tergitol 15-S-7 (nonionic): 00.20%
Triton CG-110 (nonionic): 00.55%
Fluorosurfactant (2.5%): 01.10%
Chlorhexidine Gluconate: 02.17%
Methylene Blue Chloride (1%): 00.01%

Comparative Example 3

Bleach [6% Sodium Hypochlorite (NaOCl)] 97.50%
Sodium Hydroxide (50%): 02.00%
Distilled Water: 00.50%

Comparative Example 4

Distilled Water: 97.99%
Methylene Blue Chloride (1%): 00.01%
Chlorhexidine Gluconate: 02.00%

The characteristics of the solutions were compared and recorded in the following table. The leveling and wettability were determined by evenly coating a pre-determined area of flat glass surface with a pre-determined amount of milliliters of each Comparative Example at 25° C. The coated film was observed for its continuity and maintenance of its leveling characteristic for a period of 60 seconds.

Suspension and emulsification characteristics were determined by placing a sample of 20 milliliters of each Comparative Example in a 100 mL graduated cylinder. Into each sample, ten drops of household oil were introduced into the graduated cylinders. The cylinder was inverted twenty-four times vigorously at room temperature, and the samples were observed when the cylinders were in the upright position until the separation of suspension and emulsification occurred. The surface tension of each sample was tested twice. The occurrence of separation was timed in minutes.

TABLE 1

| | Comp. Ex. 1 | Comp. Ex. 2 | Comp. Ex. 3 | Comp. Ex. 4 |
|---|---|---|---|---|
| Surface Tension (Dynes/cm) | 30.4<br>29.0 | 26<br>26.3 | 39<br>38 | 47<br>46 |
| pH | 12.75 | 5.95 | 12.50 | 5.64 |
| Leveling and Wettability | 100% | 100% | 85% | 80% |
| Suspension and Emulsification | 3 minutes | 2 minutes 45 seconds | 1 minute 4 seconds | 1 minute 15 seconds |
| Conductivity (mS/cm) | 128-133 | 1590 | Not Tested | 1522 |

As indicated in the table, Comparative Examples 1 and 2, formulated according to the present invention have superiority qualities and properties over the Comparative Examples 3 and 4, specifically the qualities of surface tension, leveling and wettability, suspension and 15 emulsification and conductivity. As the surface tension of a solution is lowered (given in dynes per centimeter for Comparative Examples 1 and 2), the ability of the solution to effectively wet the exposed surface is increased. The presence of the different surface active agents in Comparative Examples 1 and 2 contribute in producing superior performance of Comparative Examples 1 and 2 over the performance of Comparative Examples 3 and 4 (standard solutions).

Products

The potential products that the solutions could be used with are numerous. For instance, the solutions can be used during medical and dental procedures, used for disinfecting medical and dental equipment, used for cleaning and declogging water lines and pipes. The solutions could also be incorporated into general cleaning solutions, individual wipes, towels and towelettes, as sprays and other disinfectants, as hand sprays and hand sanitizers and many other cleaning, disinfecting, and treatment solutions.

Wet Surface Disinfectant

Solutions according to the present invention have been developed to act as surface disinfectants or disinfectant sprays. The disinfectants generally comprise an aqueous solution comprising surfactants in combination with a chlorhexidine compound. More specifically, the solution comprises a chlorhexidine gluconate compound in combination with surfactants, with the formula being like that shown in Comparative Example 2, above. It has been determined that the chlorhexidine gluconate compound in the disinfectant could make up to about 20% of the solution and provide a stable solution that will have desirous disinfectant effects.

Disinfectant Wipes

Disinfectant wipes can be formed using the solutions according to the present invention. FIGS. 19-22 demonstrate a method for forming a disinfectant wipe incorporating solutions according to the present invention. Preferably, wipes are impregnated with the chlorhexidine gluconate solutions according to the present invention.

Figure 19:
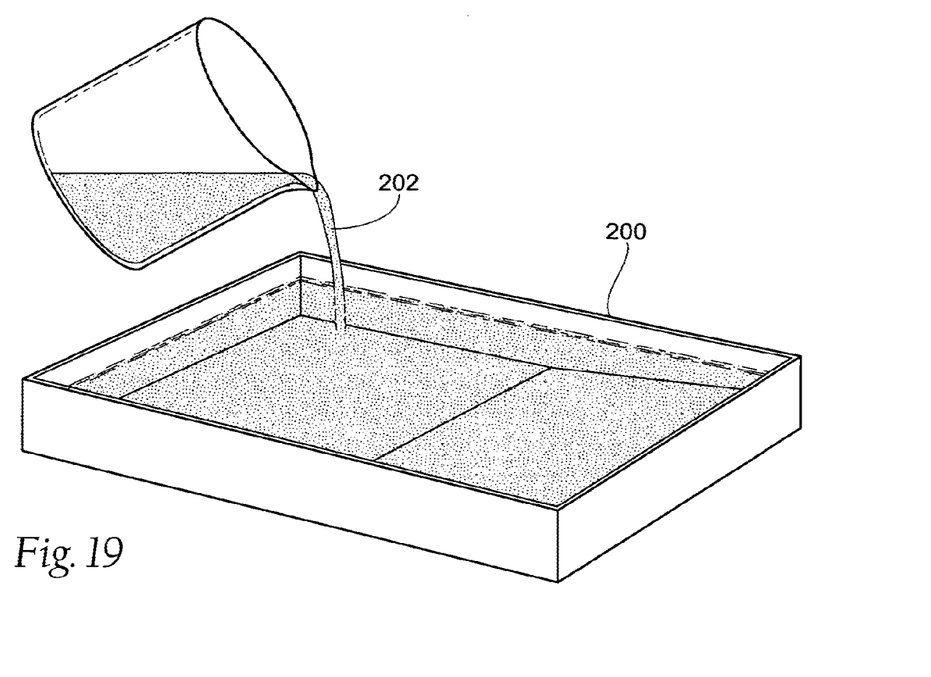
FIGS. 19-22 demonstrate a method of producing a disinfectant wipe that incorporates a solution produced in accordance with the present invention.
Figure 20:
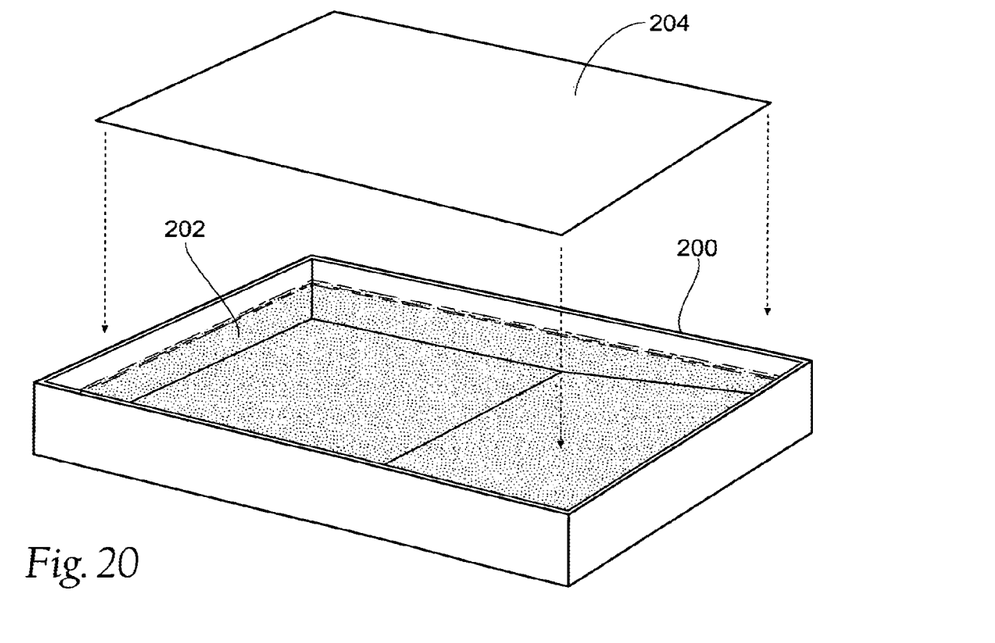

In FIG. 19, a flat container 200 is filled with a solution 202 formed according to the present invention. One example of a container is a basin generally used when painting with a paint roller. A non-woven fabric 204 is placed within the container 200, as shown in FIG. 20, and the fabric 204 soaks up the solution 202. The fabric 204 is removed from the container, and any excess solution 202 is removed from the fabric 204.

Figure 21:
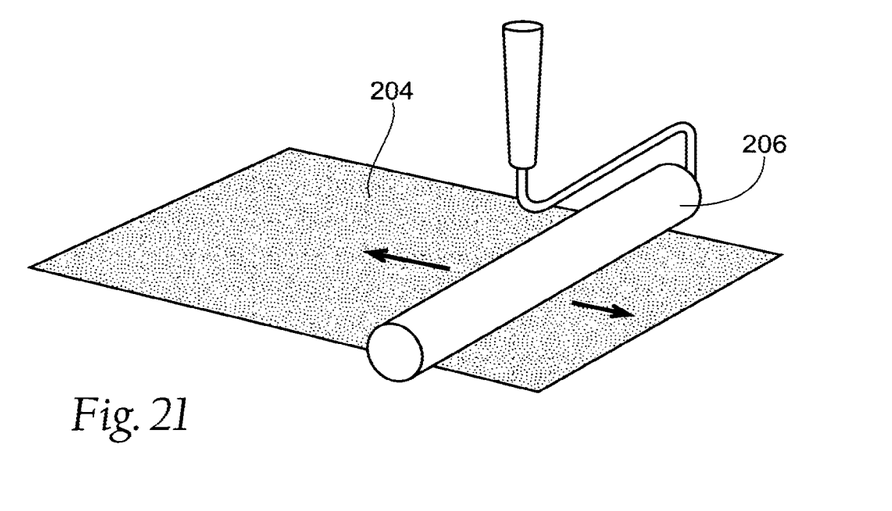

For example in FIG. 21, a paint roller 206 is used to remove the excess solution. That is, the paint roller 206 is moved back and forth over the fabric 204, thereby providing a squeegee effect to remove excess solution from the fabric 204.

Figure 22:
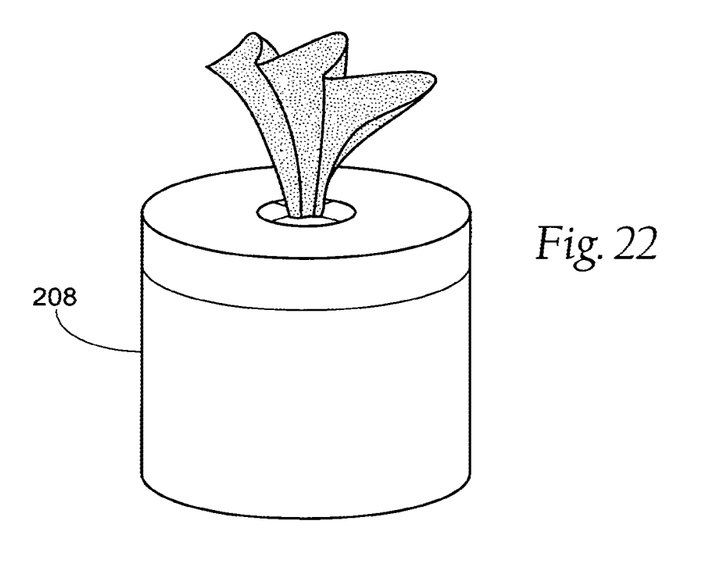

In FIG. 22, the fabric is then placed in a container 208 that will prevent the fabric 204 from drying out. It is understood that any commercially available container known and used in the industry will suffice as the container 208. It is further understood that the described process is merely exemplary of a process for making a disinfectant wipe. It is further understood that other processes known and used in the industry, especially processes for mass producing wipes, can be employed to produce wipes according to the present invention.

Semi-Anhydrous Surface Disinfectant

Drying style disinfectant sprays have also been formulated according to the present invention. The formulas are generally the same as the wet surface disinfectants, with a portion of the water, a polar solvent, in the solution being replaced with an alcohol compound. For example, the formula shown above in Comparative Example 2 would be similar for a dry disinfectant, except a portion of the distilled water would be replaced with an alcohol compound. In one preferred embodiment, approximately ~70% of the distilled water would be replaced with an alcohol compound, preferably, denatured ethanol 40-B, with approximately ~25% distilled water remaining in the formula. In a preferred embodiment, the solution will comprise approximately 5% water with an alcohol content between 68% and 95% of the solution. In a more preferred embodiment, the alcohol content will be between 70% and 85% of the solution. As is known in the art, various mixtures of alcohols and denaturants may generally be used.

Semi-Anhydrous Wipe

Semi-anhydrous, or dry wipes, are formed similar to the wet wipes, except that the wipes would be impregnated with the semi-anhydrous surface disinfectant as opposed to the wet surface disinfectant. Semi-anhydrous wipes would be formed similar to that described for the wet wipes.

The present invention embodies improved solutions that can be employed for a wide variety of uses. Further, wide range of the solutions can be incorporated into a products. Provided that a solution formulated according to the present invention is used for cleaning and disinfecting purposes, it is understood that the solution and the medium used would fall within the scope of the present invention.

The present invention provides classes of disinfectants and irrigants that combine surfactants in a manner so that the surfactants will complex with one another and, also, with the main disinfectant of the solution. Provided that the discussed solutions, surfactants, and other compounds complex with one another, it is understood that such combinations in a wide range of percentages will fall within the scope of the present invention.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

The invention claimed is:

1. A stable irrigant and disinfectant solution that does not gel or clot, the stable solution obtained in a process comprising the steps of:
   combining an ethoxylate surfactant with water and agitating to provide a first mixture;
   adding to the first mixture an alkyl polyglucoside surfactant and agitating to provide a second mixture;
   adding to the second mixture a fluorosurfactant and agitating to provide a tertiary surfactant system;
   adding to the tertiary surfactant system an aqueous solution comprising a chlorhexidine-based compound in a form selected from the group consisting of a gluconate, an acetate, and a hydrochloride, to form a complex with one another;
   adding to the complex of the surfactant and the chlorhexidine-based compound a chelating agent in an amount that does not form a white precipitate of flocculant, the chelating agent selected from the group consisting of ethylenediaminetetracetic acid (EDTA) and citric acid, and agitating to obtain the stable irrigant and disinfectant solution,
   wherein in the irrigant and disinfectant solution the chlorhexidine based-compound is provided at about 0.1-20.0 weight percent , the ethoxylate surfactant is provided at about 0.1-2.0 weight percent, the alkyl polyglucoside is provided at about 0.1-2.0 weight percent, and the fluorosurfactant is provided at about 0.01-2.0 weight percent.

2. The irrigant and disinfectant solution according to claim 1 comprising, by weight percent, the chlorhexidine-based compound at about 0.1-4.0% .

3. The irrigant and disinfectant solution according to claim 1 wherein said chlorhexidine-based compound comprises chlorhexidine gluconate.

4. The irrigant and disinfectant solution according to claim 1 wherein the chelating agent comprises EDTA.

5. The irrigant and disinfectant solution according to claim 1 wherein the chelating agent comprises citric acid.

6. The irrigant and disinfectant solution according to claim 4, wherein the EDTA is provided at about 1% by weight of the irrigant and disinfectant solution.

7. The irrigant and disinfectant solution according to claim 5, wherein the citric acid is provided at about 2% by weight of the irrigant and disinfectant solution.

8. The irrigant and disinfectant solution according to claim 1 wherein the ethoxylate surfactant comprises an alkylphenol, phenol, or alcohol ethoxylate surfactant.

* * * * *